United States Patent [19]
Denton

[11] Patent Number: 5,591,130
[45] Date of Patent: Jan. 7, 1997

[54] ESOPHAGEAL INTUBATION DETECTOR WITH INDICATOR

[75] Inventor: Marshall T. Denton, Salt Lake City, Utah

[73] Assignee: Wolfe Troy Medical, Inc., Salt Lake City, Utah

[21] Appl. No.: 484,936

[22] Filed: Jun. 7, 1995

Related U.S. Application Data

[63] Continuation-in-part of Ser. No. 199,628, Feb. 22, 1994, Pat. No. 5,487,731.

[51] Int. Cl.$^6$ ............................................. A61M 29/00
[52] U.S. Cl. ............... 604/100; 128/202.22; 128/207.15
[58] Field of Search ..................... 604/100; 128/200.24, 128/200.26, 202.22, 205.23, 207.14, 207.15

[56] References Cited

U.S. PATENT DOCUMENTS

| | | |
|---|---|---|
| D. 277,782 | 2/1985 | Beck . |
| D. 277,783 | 2/1985 | Beck . |
| D. 277,889 | 3/1985 | Beck . |
| 2,638,096 | 5/1953 | Waldhaus . |
| 3,991,762 | 11/1976 | Radford . |
| 4,119,101 | 10/1978 | Igich . |
| 4,346,702 | 8/1982 | Kubota . |
| 4,593,689 | 6/1986 | White . |
| 4,595,005 | 6/1986 | Jinotti . |
| 4,691,702 | 9/1987 | Chantzis . |
| 4,696,296 | 9/1987 | Palmer . |
| 4,805,611 | 2/1989 | Hodgkins . |
| 4,825,859 | 5/1989 | Lambert . |
| 4,879,999 | 11/1989 | Leiman et al. . |
| 4,938,210 | 7/1990 | Shene . |
| 4,938,741 | 7/1990 | Lambert . |
| 4,981,466 | 1/1991 | Lumbert . |
| 5,054,482 | 10/1991 | Bales . |
| 5,056,514 | 10/1991 | Dupont . |
| 5,125,893 | 6/1992 | Dryden . |

(List continued on next page.)

OTHER PUBLICATIONS

The capnographer discussed on pp. 2 and 3 of the specification.
The Easy Cap End–Tidal $CO_2$ detector discussed on p. 3 of the specification.
Two page instructions for the "Esophageal Intubation Detector (EID)" prepared by Wolfe Tory Medical, Inc. in 1993.
510(k) Notification from Wolfe–Carney Medical for market clearance from the Food and Drug Administration, dated Feb. 8, 1993, 32 pages.

(List continued on next page.)

*Primary Examiner*—Randall L. Green
*Assistant Examiner*—Perry E. Van Over
*Attorney, Agent, or Firm*—Trask, Britt & Rossa

[57] ABSTRACT

An esophageal intubation detector with an indicator is used to determine whether the hollow tip of an endotracheal tube is in the esophagus or trachea of a patient. In a preferred embodiment, the esophageal intubation detector includes a syringe (or a bulb) connected to the endotracheal tube through an adapter to which the indicator is connected. The bulb may be associated with a resuscitator bag. A clinician places the endotracheal tube into, for example, a patient's mouth and throat. The esophageal intubation detector is connected to the endotracheal tube creating a system. The system volume increases through retraction of a syringe plunger or self-inflation of a depressed bulb. If the tube tip is in the esophagus, the tube tip will become occluded with the walls of the esophagus as the system volume increases, causing the system pressure to decrease and causing activation of the indicator, implying that the endotracheal tube is in the esophagus. By contrast, if the tube tip is in the trachea, the tube tip remains open as the system volume increases and free aspiration of air occurs. The system pressure remains relatively constant and the indicator is not activated, implying the endotracheal tube is in the trachea. Activation of the indicator may result in audible or visual (or both) signs to inform the clinician of the position of the tube tip.

39 Claims, 14 Drawing Sheets

U.S. PATENT DOCUMENTS

| | | |
|---|---|---|
| 5,134,996 | 8/1992 | Bell . |
| 5,135,488 | 8/1992 | Foote et al. . |
| 5,163,904 | 11/1992 | Lampropoulos et al. . |
| 5,279,289 | 1/1994 | Kirk . |
| 5,287,848 | 2/1994 | Cubb et al. . |
| 5,309,902 | 5/1994 | Kee et al. . |
| 5,329,940 | 7/1994 | Adair . |
| 5,331,967 | 7/1994 | Akerson . |
| 5,339,808 | 8/1994 | Don Michael . |
| 5,360,003 | 11/1994 | Capistrano . |
| 5,368,017 | 11/1994 | Sorenson et al. . |
| 5,513,628 | 5/1996 | Coles et al. . |

OTHER PUBLICATIONS

B. A. MacLeod et al., "Verification of Endotracheal Tube Placement With Colorimetric End–Tidal $CO_2$ Detection," Annals of Emergency Medicine, 20:3 Mar. 1991, pp. 267–270 (78–81).

M. Y. K. Wee, "The Oesophageal Detector Device: Assessment of a New Method to Distinquish Oesophageal from Tracheal Intubation," Anaesthesia, 1988, 43:27–29.

K. N. Williams et al., "The Oesophageal Detector Device: A Prospective Trial of 100 Patients," Anaesthesia, 1989, 44:412–14.

S. T. Sum Ping et al., "Accurancy of the FEF $CO_2$ Detector in the Assessment of Endotracheal Tube Placement," Anesth Analg, 1992;74:415–19.

W. R. Anton et al., "A Disposable End–Tidal $CO_2$ Detector to Verify Endotracheal Intubation," Annals of Emergency Medicine, 20:3 Mar. 1991, pp. 271–75 (82–86).

R. G. Foutch et al., "The Esophageal Detector Device: A Rapid and Accurate Method for Assessing Tracheal Versus Esophageal Intubation in a Porcine Model," Annals of Emergency Medicine, Sep. 1992, 21:9, pp. 1073–1076 (43–46).

J. J. O'Leary, "A Method of Detecting Oesophageal Intubation or Confirming Tracheal Intubation," Anaesth Intens Care (1988), 16, pp. 299–301.

W. A. Jenkins et al., "The Syringe Aspiration Technique to Verify Endotracheal Tube Position," from NAEMSP Abstracts, presented Jun. 19, 1992, Abstract in Prehospital and Disaster Medicine, 1992, vol. 7, Suppl. 1, 12S.

D. Oberly et al., "An Evaluation of the Esophageal Detector Device Using a Cadaver Model," Amer. J. of Emergency Medicine, vol. 10, No. 4, Jul. 1992, pp. 317–320.

P. L. Donahue, "The Oesophageal Detector Device", Anaesthesia, 1994, vol. 49, pp. 863–865.

W. A. Jenkins et al., "The Syringe Aspiration Technique to Verify Endotracheal Tube Position" American Journal of Emergency Medicine, Jul. 1994, vol. 12, No. 4, pp. 413–415.

W. P. Bozeman et al., "The Esophageal Detector Device Versus End Tidal $CO_2$ Detection in Emergency Intubations," from SAEM 1994 Annual Meeting Abstracts, 1994, 1(2) A77, #232 (Abstract in Academic Emerg Med).

K. H. Andersen et al., Forum "Assessing the position of the tracheal tube. The reliability of different methods." Anaesthesia, 1989, vol. 44, pp. 984–985.

Linda Zaleski et al., "The Esophageal Detector Device, Does It Work?", Anesthesiology, 1993, 79:244–47.

M. R. Salem et al., "Use of the Self–Inflating Bulb for Detecting Esophageal Intubation After Esophageal Ventilation," Anesth Analg, 1993, 77:1227–31.

M. R. Salem et al., "Efficacy of the Self–inflating Bulb in Detecting Esophageal Intubation, Does the Presence of a Nasogastric Tube or Cuff Deflation Make a Difference?", Anesthesiology, Jan. 1994, 80:42–48.

N. S. Morton et al., "The Oesophageal Detector Device: Successful Use in Children," Correspondence, Anaesthesia, 1989, 44:523–24.

A. Baraka et al., "The Esophageal Detector Device in the Morbidly Obese," Letters to the Editor, Anesth Analg, 1993, 77(2):400.

M. K. Y. Wee, "Comments on the Oesophageal Detector Device," Correspondence, Anaesthesia, 1989, 44:930–31.

A. Baraka, "The Oesophageal Detector device in the asthmatic patient," Correspondence, Anaesthesia, 1993, 48(3):275.

S. R. Haynes et al., "Use of the oesophageal detector device in children under one year of age," Anaesthesia, 1990, vol. 45, pp. 1067–1069.

Y. L. Burnett et al., "Efficacy of the Self–inflating bulb in verifying tracheal tube placement in children." Abstract in Anesth Analg 1995;80;S63.

P. K. Sood et al., The Esophageal detector device: Ellick's evacuator versus syringe [Letter]. Anesthesiology 1995;82:314.

Y. Wafai et al. "The self–inflating bulb in detecting esophageal intubation: Effect of bulb size and technique used." Abstracts in Anesthesiology 1993;79(3A):A496.

Y. Wafai et al., "The self–inflating bulb for confirmation of tracheal intubation: Incidence and demography of false negatives." Abstract in Anesthesiology 1994;81(3A):A1304.

M. R. Salem et al., Comments on the self–inflating bulb [Letter]. Anesthesiology 1995;82:315–316.

Y. Wafai et al., "Effectiveness of the self–inflating bulb for verification of proper placement of the esophageal tracheal combitube." Anesth Analg 1995;80:122–126.

W. H. Petroianu et al., Detection of an oesophageal intubation: State of the art [Letter]. Anaesth Intensive Care 1994;22(6):744–746.

P. Clyburn et al., Accidental oesophageal intubation. Br J Anaesth 1994;73:55–63.

CD Marley et al.: Evaluation of a prototype esophageal detection device. Acad Emerg Med 1995;2:503–507.

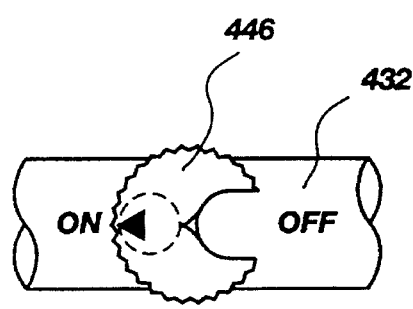
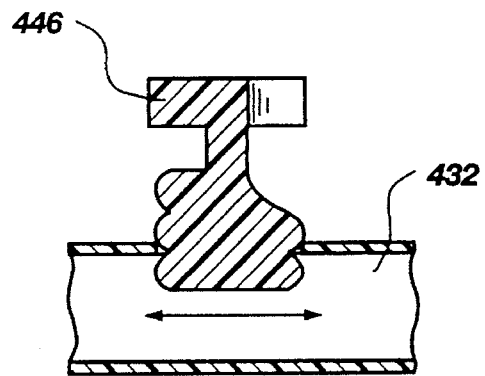
Fig. 19A                    Fig. 19B
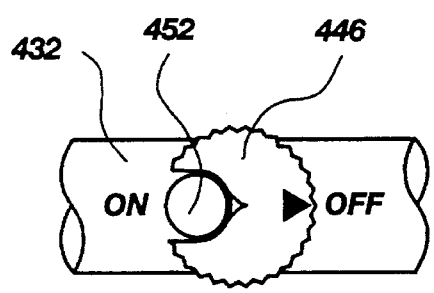
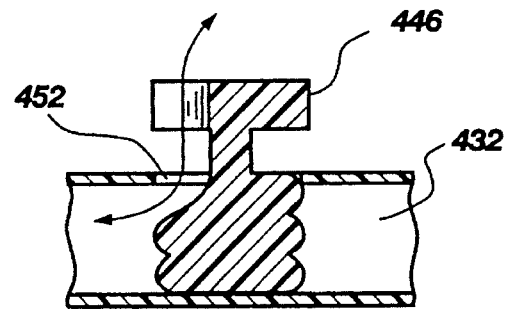
Fig. 20A                    Fig. 20B

ESOPHAGEAL INTUBATION DETECTOR WITH INDICATOR

RELATED APPLICATION

This application is a continuation-in-part of application Ser. No. 08/199,628 filed Feb. 22, 1994 now U.S. Pat. No. 5,487,731.

BACKGROUND OF THE INVENTION

1. Field of the Invention

The present invention relates to an esophageal intubation detector and, more particularly, to an esophageal intubation detector with an indicator that indicates whether an endotracheal tube (or other tubular airway controlling device) is in a patient's esophagus or in the patient's trachea, immediately following an attempted intubation.

2. State of the Art

Endotracheal tubes may be used to pump oxygen enriched air into the lungs of a patient. The procedure is used in the operating room, the emergency department, and pre-hospital care settings, such as accident sites. One end of the endotracheal tube is connected to a source of oxygen and the other end is placed in the patient's trachea, in a procedure referred to as intubation. A danger in intubation is that the endotracheal tube may be placed in the esophagus rather than the trachea. Even an experienced clinician has difficulty in properly placing the endotracheal tube. Improper placement of the tube may result in permanent injury or death. Accordingly, detection of improper placement of the endotracheal tube is extremely important.

Clinical examination alone is dependent on the clinician's experience and judgement and may give misleading results. For this reason, accessory devices exist that help determine if the trachea is properly intubated. For example, capnographers have been used to detect improper placement. A capnographer is an expensive instrument that detects the presence of $CO_2$. Confirmation of proper endotracheal tube placement is based on the fact that carbon dioxide is present in exhaled air in approximately 5% concentration, but is present in esophageal gas in only minute concentrations. The capnographer is a relatively large, sophisticated, and expensive reusable instrument that has a valid use in hospital operating rooms. The capnographer is too bulky, too expensive, and requires too much time to calibrate for routine use in prehospital settings and emergency departments. Unfortunately, it is these settings where experience may be limited and where esophageal intubations more frequently occur.

The EASY CAP End-Tidal $CO_2$ detector is a currently available disposable device for use outside the operating room that assists in distinguishing esophageal from tracheal intubations by a color indication. The EASY CAP End-Tidal $CO_2$ detector is marketed by Nellcor Inc. (formerly produced and distributed by FENEM Airway Management Systems under the name "FEF End-Tidal $CO_2$ detector"). After intubation is performed, the $CO_2$ detector device is attached to the endotracheal tube in line with the oxygen bag. Oxygen is insufflated through the device into the endotracheal tube and lungs, then exhaled back through the device. A change of color from purple to yellow with each breath indicates tracheal intubation. If the endotracheal tube is in the esophagus, no $CO_2$ is detected and the color change does not occur.

The $CO_2$ detector device will not easily detect tracheal intubation in the patient who is pulseless or inadequately perfusing the pulmonary circulation. This is due to inadequate $CO_2$ exhalation. It will still detect esophageal intubation in these patients. However, many tracheal intubations will be interpreted as esophageal due to lack of color change. Clinical judgement is required in these cases.

Another technique for distinguishing esophageal from tracheal intubation is described in M. Y. K. Wee, "The oesophageal detector device assessment of a new method to distinguish oesophageal from tracheal intubation," *Anaesthesia*, 43:27–29 (1988). This technique relies on the relative rigidity of the tracheal wall, as compared to that of the esophagus. The trachea remains constantly patent due to C-shaped rings of cartilage supporting its lumen. The esophagus will collapse over the end of a rigid tube when significant negative pressure (with respect to atmospheric pressure) is applied in the tube, thus preventing aspiration of air. The more rigid trachea, on the other hand, remains open and allows free aspiration of air, when significant negative pressure is applied in the tube.

Under the technique, a detector device includes a syringe that is attached to an adaptor. After intubation, the adaptor is connected to the endotracheal tube. Air is aspirated into the syringe by pulling the syringe plunger. Free flow of air (i.e., ease in pulling the syringe plunger) is indicative of proper tube placement in the trachea. Resistance to flow (i.e., resistance to pulling the syringe plunger) indicates that the endotracheal tube may be improperly placed.

SUMMARY OF THE INVENTION

An intubation detector system including an indicator provides an indication of whether a tubular airway controlling device, such as an endotracheal tube, is in a patient's esophagus or trachea. In one embodiment of the invention, an esophageal intubation detector includes a syringe that is connected to the endotracheal tube through an adapter.

The adapter includes an orifice over which an indicator is positioned. The indicators may be activated in response to a significant pressure differential across the indicator. A variety of indicators, including audible, visual, and transducer indicators, may be used. The indicators may provide an audible, visual, tactile, and/or electrical signal indicating the position of the endotracheal tube. Some indicators may only provide signals indicating the endotracheal tube is in the esophagus. The clinician infers that the endotracheal tube is in the trachea from the absence of the signal. Other indicators may provide signal(s) that positively indicate that the endotracheal tube is in the trachea, and/or the signal(s) from the indicator may be processed to positively indicate that the endotracheal tube is in the trachea.

The present invention is not limited to using a syringe, but may include other sources of negative pressure. For example, a bulb may be a volume changing device. The bulb may be used in connection with a resuscitator bag. Following being squeezed, the bulb increases volume by returning to its natural shape.

In operation, a clinician inserts an endotracheal tube into the mouth or nose and throat of a patient. The tip of the endotracheal tube includes holes. With the syringe plunger pushed toward the tip of the syringe, the clinician connects the syringe (or other volume changing device) to the endotracheal tube, creating a "system" having a system volume and a system pressure. The clinician then pulls the plunger away from the syringe tip causing the system volume in the esophageal intubation detector and endotracheal tube to increase. The device causes the total system volume to expand, either through retraction of the syringe plunger or self inflation of the cavity. If the tip of the endotracheal tube is within the esophagus, this volume expansion leads to occlusion of the hollow tip of the endotracheal tube by the walls of the esophagus. The result is a decrease in system pressure. Once this pressure decrease surpasses a predetermined level, the indicator is activated either through pressure transducer triggering or via airflow through the indicator. Activation of the indicator in the above-described embodiment implies that the endotracheal tube is in the esophagus. By contrast, if the distal tip of the endotracheal tube is placed within the trachea, the tube tip is not occluded during system volume expansion and free aspiration of air occurs. The pressure within the system remains relatively constant and the indicator is not activated. This finding implies that the endotracheal tube is in the trachea.

The present invention may be used with both vented and non-vented indicators. In the case of a vented indicator, the system pressure may suddenly increase when the plunger seal passes the orifice. The indicator may be activated by detection of a change in the pressure or by flow of air created by the pressure differential.

The indicator may provide signals to a remote audio and/or visual communication device.

In the embodiment in which the resuscitator bag is used, the detection system may include a bulb connected to the endotracheal tube through a connecting tube and adapter. The connecting tube may include a venting ON-OFF switch that deactivates the detection system following proper intubation.

BRIEF DESCRIPTION OF THE DRAWINGS

FIG. 19A shows a top view of a vent switch of the intubation detector/resuscitator system of FIGS. 18A and 18B in the ON position.

FIG. 19B shows a side view of the vent switch of FIG. 19A in the ON position.

FIG. 20A shows a top view of the vent switch of FIG. 19A in the OFF position.

FIG. 20B shows a side view of the vent switch of FIG. 19A in the OFF position.

DETAILED DESCRIPTION OF PREFERRED EMBODIMENTS

A. Syringe-Based Detection Systems

1. Embodiments of Detectors and Audio Indicators

Figure 1:
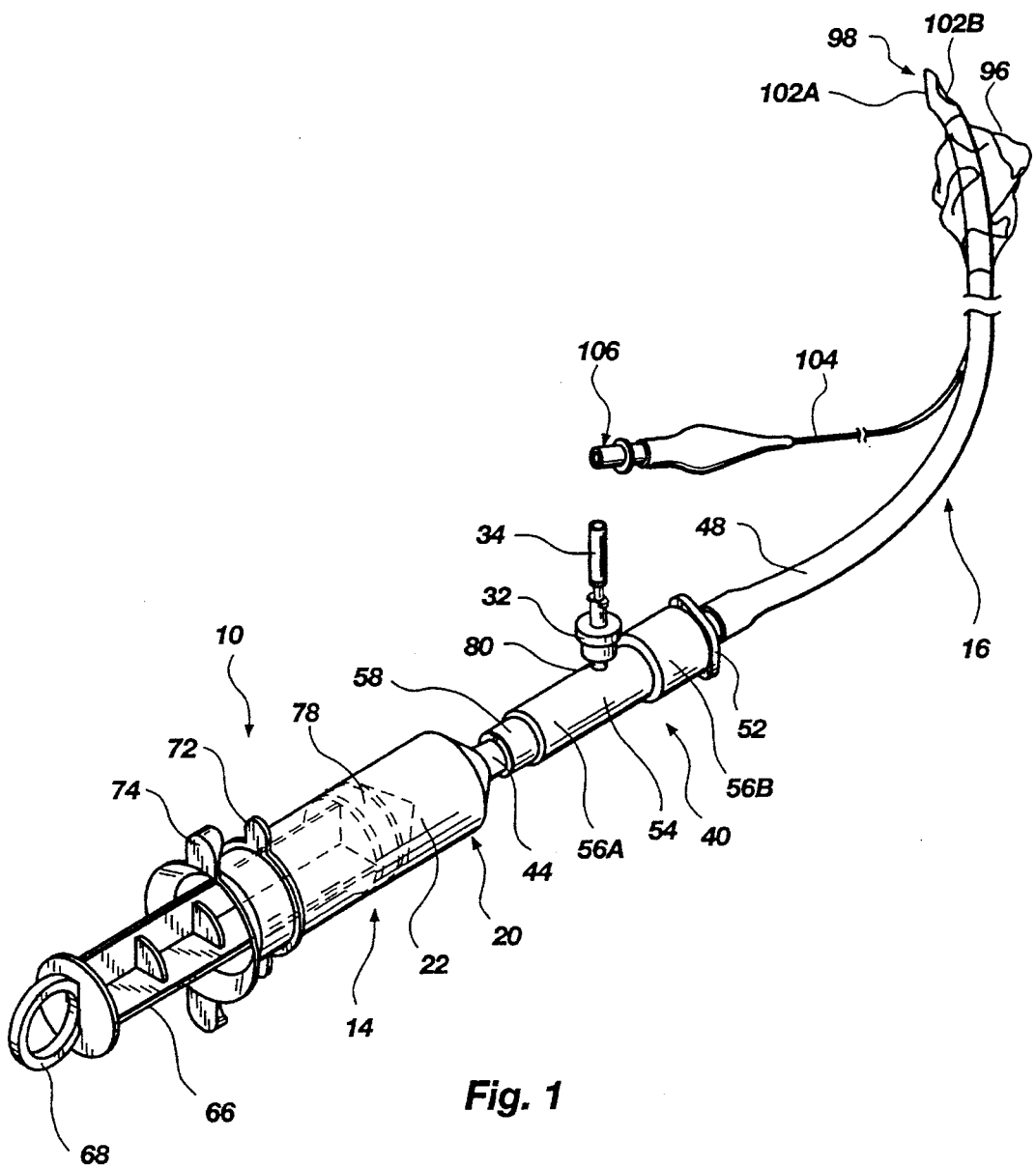
FIG. 1 is a perspective view of a first embodiment of an esophageal intubation detector including a first embodiment of an audible indicator and connected to an endotracheal tube.
Figure 2:
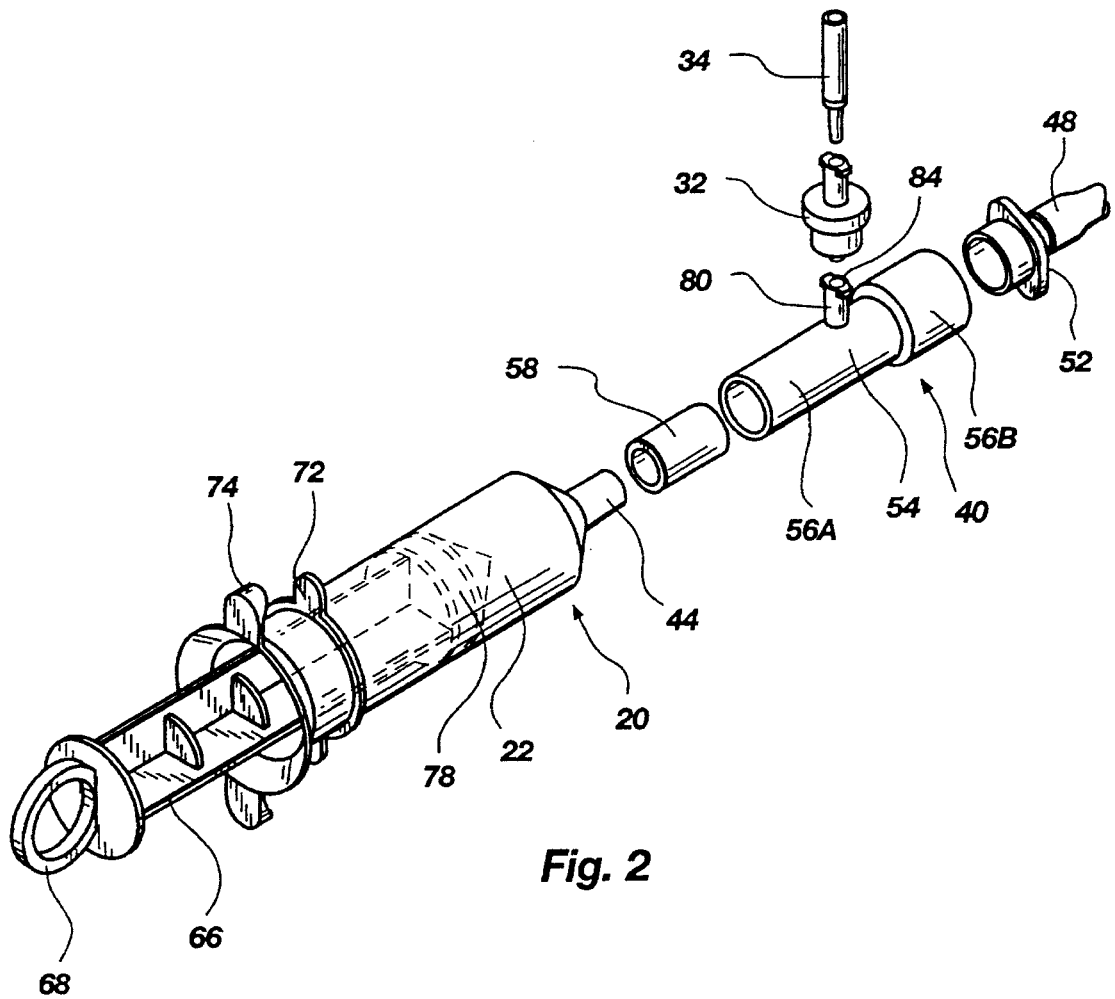
FIG. 2 is an exploded view of the esophageal intubation detector of FIG. 1 and a portion of the endotracheal tube.

Referring to FIGS. 1 and 2, in a first embodiment of the present invention, an esophageal intubation detection system 10 includes an esophageal intubation detector 14 and an endotracheal tube 16. In this first embodiment, esophageal intubation detector 14 includes a syringe such as standard catheter tip syringe 20 and an adapter 54 on which an indicator is positioned.

As described herein, a variety of indicators may be used. In the embodiment of FIGS. 1 and 2, the indicator is an audible indicator 32. Audible indicator 32 is shown with an optional sound enhancer 34 which increases the loudness of the sound from audible indicator 32. The length and diameter of sound enhancer 34 is chosen such that the sound in the combination of audible indicator 32 and sound enhancer 34 obtains resonant frequency. This results in a significant increase in the decibel output of the indicator, making it easily detected by the human ear. Details of audible indicator 32 are provided in FIGS. 4A and 4B below. Other audible indicators are shown in FIGS. 7, 9A, 9B, and 16.

Figure 3:
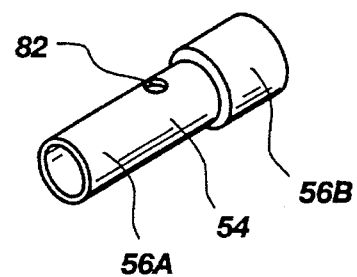
FIG. 3 is a perspective view of an adapter of the esophageal intubation detector of FIG. 1.

Referring to FIGS. 1–3, esophageal intubation detector 14 is connectable to endotracheal tube 16 by means of an adapter 40. It is contemplated that esophageal intubation detector 14 and endotracheal tube 16 may be sold separately or together, and if sold together, in a connected or disconnected condition.

Adapter 40 includes a hollow two-diameter adapter 54 and a connection tube 58. Two-diameter adapter 54 includes sections 56A and 56B. One end of connection tube 58 is connected over syringe tip 44 and the other end of connection tube 58 is connected inside section 56A of two-diameter adapter 54. Of course, adapter 40 could be comprised of a greater or fewer number of components than two-diameter adapter 54 and connection tube 58. Further, it is not necessary that a two-diameter adapter be used. It is preferred that connection tube 58 is connected between syringe tip 44 and section 56A in a tight fit to prevent separation and leakage. The use of heat during assembly may facilitate the tight fit. In actual use, connection tube 58 may be completely covered by one end of section 56A, as opposed to that illustrated in FIG. 1.

Syringe 20 includes a barrel 22 and a plunger 66 having a plunger seal 78 (shown inside barrel 22). Plunger 66 may include a ring handle 68, and syringe 20 may include handles 72 and 74 for ease in moving plunger 66.

One version of endotracheal tube 16 includes a tube 48 and an end adapter 52 at one end of tube 48. Endotracheal tube 16 includes an inflatable balloon 96 and a tip 98 with holes 102A and 102B. Balloon 96 may be inflated through a tube 104 and connection port 106. Of course, the details of endotracheal tube 16 could be different without departing from the present invention.

Before intubation, plunger 66 is positioned so that plunger seal 78 is near syringe tip 44. Under one procedure, at the time of intubation, a clinician inserts tip 98 of endotracheal tube 16 into the throat of the patient. After initial intubation, the clinician connects section 56B over end adaptor 52 of endotracheal tube 16. The clinician then pulls plunger 66 away from syringe tip 44. Under another procedure, section 56B is connected to end adaptor 52 prior to initial intubation.

Referring to FIGS. 1 and 2, in a preferred embodiment, a hollow luer lock stem 80 is connected to section 56A of two-diameter adapter 54. Audible indicator 32 is connected to luer lock stem 80. Section 56A has an orifice 82 (shown in FIG. 3). Stem 80 has an orifice 84 that is open with respect to orifice 82 allowing passage of air between a lower portion of audible indicator 32 and the hollow portion of two-diameter adapter 54. Stem 80 may be originally molded or otherwise formed as an integral portion of two-diameter adapter 54 or may be inserted into orifice 82 and melted or glued thereto. Stem 80 may project partially through orifice 82. As used herein, referring to the indicator as being positioned over the orifice does not preclude the indicator from being partially inserted through the orifice.

Figure 4A:
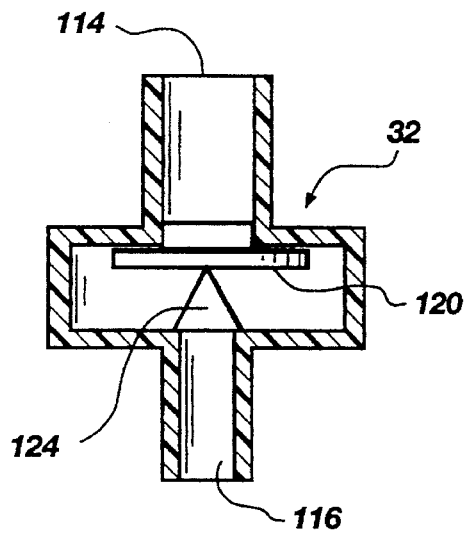
FIG. 4A is a side sectional view of the first embodiment of audible indicator.
Figure 4B:
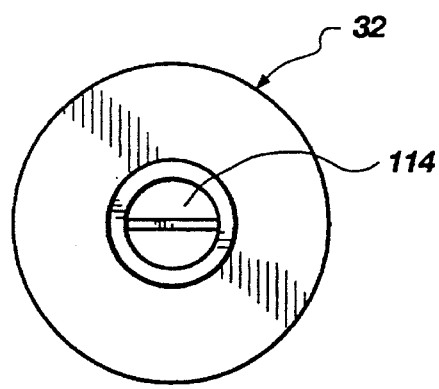
FIG. 4B is a top view of the first embodiment of audible indicator shown in FIG. 4A.

FIGS. 4A and 4B show side and top views of audible indicator 32. Audible indicator 32 includes an orifice 114 and an orifice 116, which are aligned with orifice 84 (such as by any of the ways described in connection with stem 80 and orifice 84). When the difference in air pressures in orifice 114 and 116 equals a "crack pressure," a disk 120 vibrates on a stand 124 and thereby produces a sound. Merely by way of example, and not limitation, the crack pressure of audible indicator 32 is minus 1.5 to minus 5.0 psi. Various indicators will have different crack pressures.

As used herein, the volume in barrel 22, adapter 40, and tube 48 between plunger seal 78 and tip 98 of endotracheal tube 16 is referred to as the "system volume." The air pressure (psi) in barrel 22, adapter 40, and tube 48 between plunger seal 78 and tip 98 is referred to as the "system pressure." If intubation is proper, the system pressure remains essentially constant as plunger 66 is pulled away from syringe tip 44. Accordingly, the pressure differential across audible indicator 32 remains essentially constant.

On the other hand, if intubation is not proper, tip 98 becomes occluded, and the system pressure decreases as plunger 66 is pulled away from syringe tip 44. The system pressure decreases until it is less than the crack pressure of audible indicator 32. Air then passes about disk 120 causing it to vibrate. The vibration of disk 120 produces a sound indicating to the clinician that intubation may be improper. The crack pressure is reached when a significant pressure differential is achieved across audible indicator 32. As used herein, a significant pressure differential is one that activates the indicator.

Figure 5:
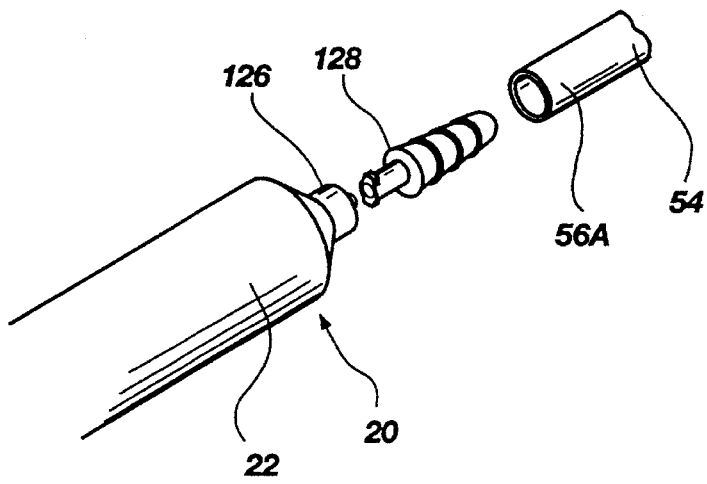
FIG. 5 is a perspective view of a luer lock structure for connecting the syringe to the adapter.

FIG. 5 illustrates an alternative structure for joining syringe barrel 22 to adapter 54. In the embodiment of FIG. 5, a luer lock syringe tip 126 connects to a luer lock connection adapter piece 128, which fits inside section 56A of adapter 54. Luer lock syringe tip 126 may be connected to luer lock connection adapter piece 128 prior to or after attempted intubation. The structure of FIG. 5 may be used with various embodiments of the esophageal intubation detection system, such as, for example, that of FIG. 1.

Figure 6A:
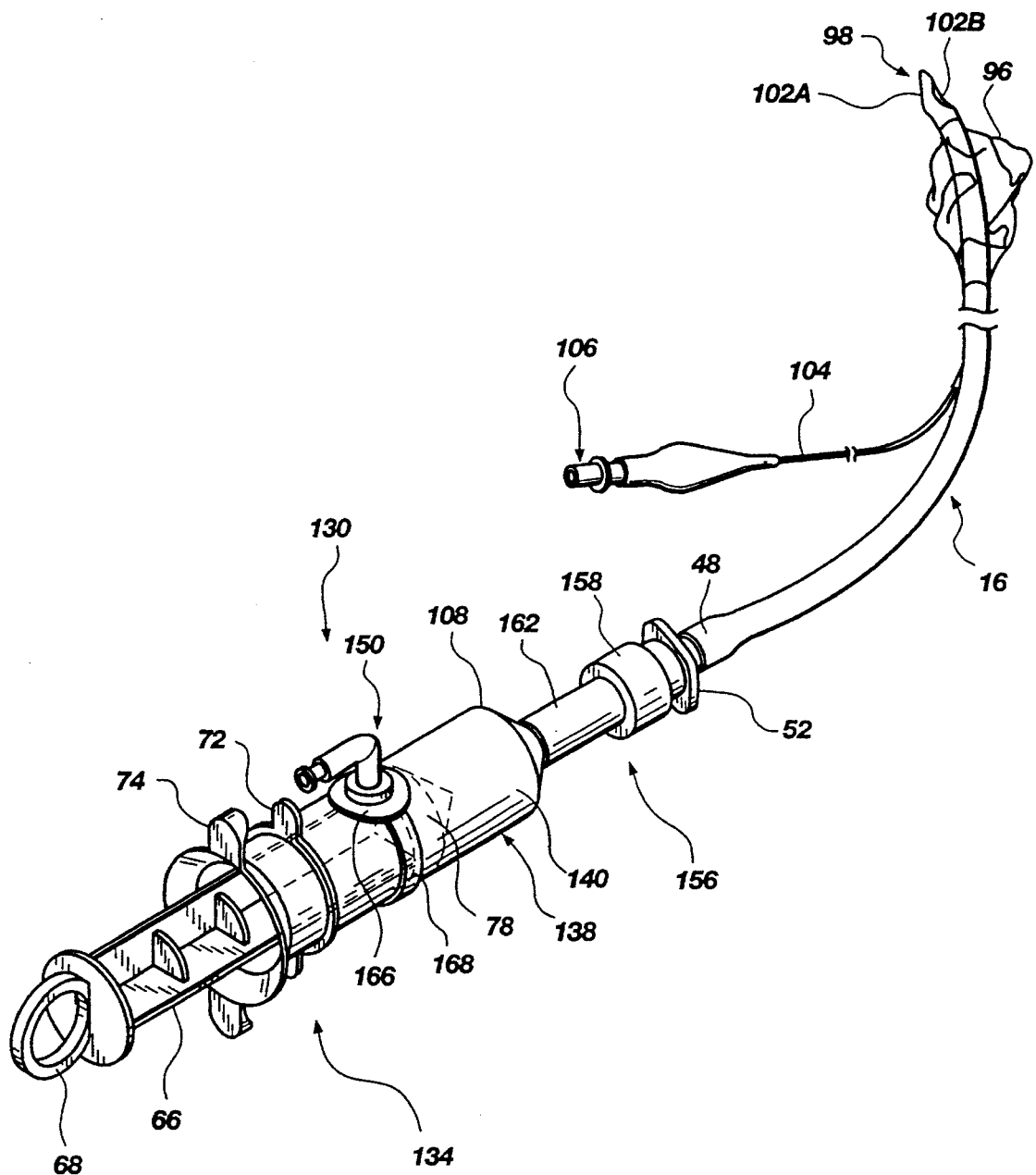
FIG 6A is a perspective view of a second embodiment of an esophageal intubation detector including a second embodiment of an audible indicator and connected to an endotracheal tube.
Figure 6B:
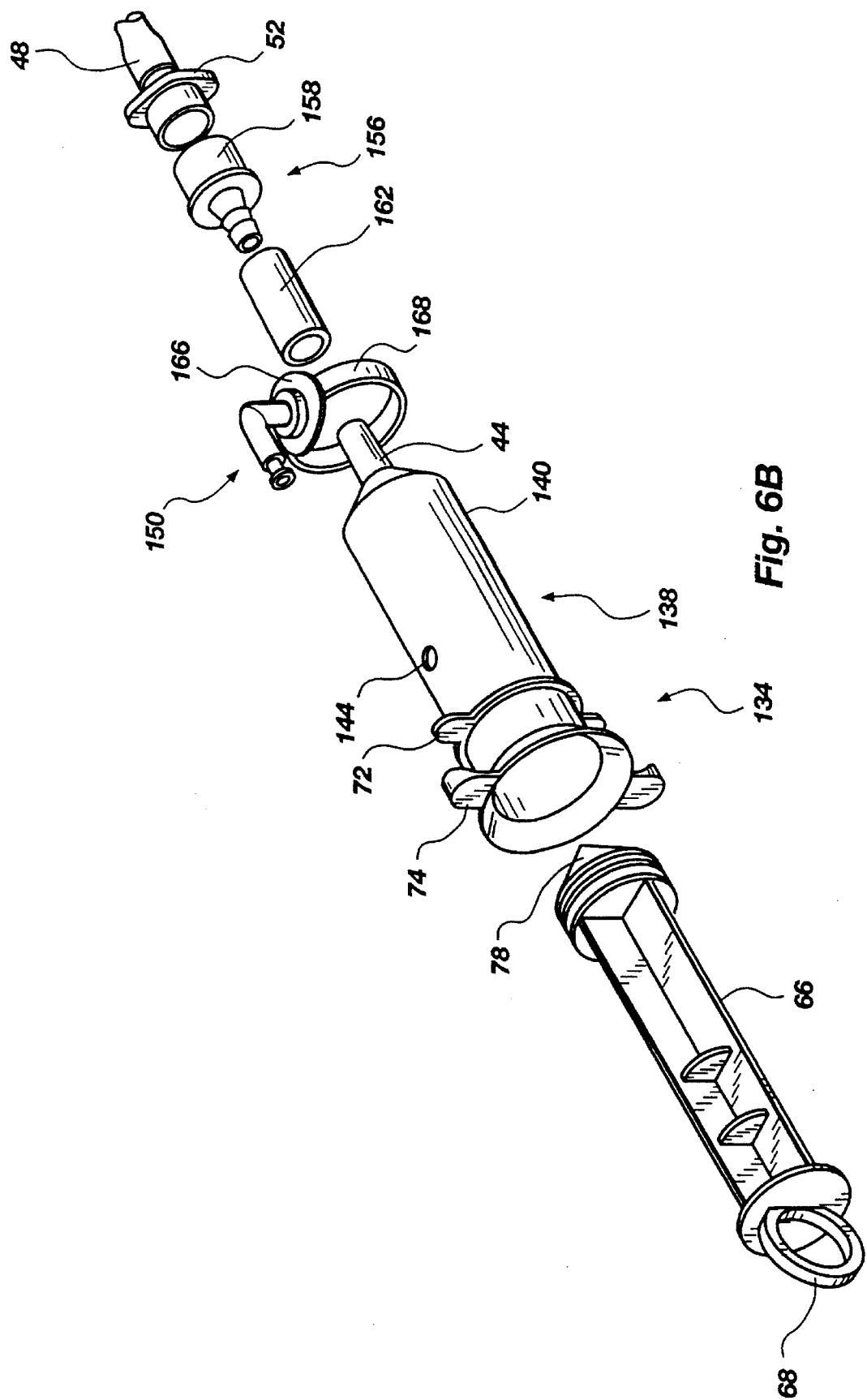
FIG. 6B is an exploded view of the esophageal intubation detector of FIG. 6A and a portion of the endotracheal tube.

Referring to FIGS. 6A and 6B, an esophageal intubation detection system 130 includes an esophageal intubation detector 134 and endotracheal tube 16 connected through an adapter 156. Esophageal intubation detector 134 includes a syringe such as standard catheter tip syringe 138 having a barrel 140. (Alteratively, the luer lock structure of FIG. 5 could be used.) In contrast to orifice 84 in two-diameter adapter 54 (shown in FIGS. 1–3), esophageal intubation detector 134 in FIGS. 6A and 6B includes an orifice 144 in barrel 140 over which an indicator is secured in place.

Figure 7:
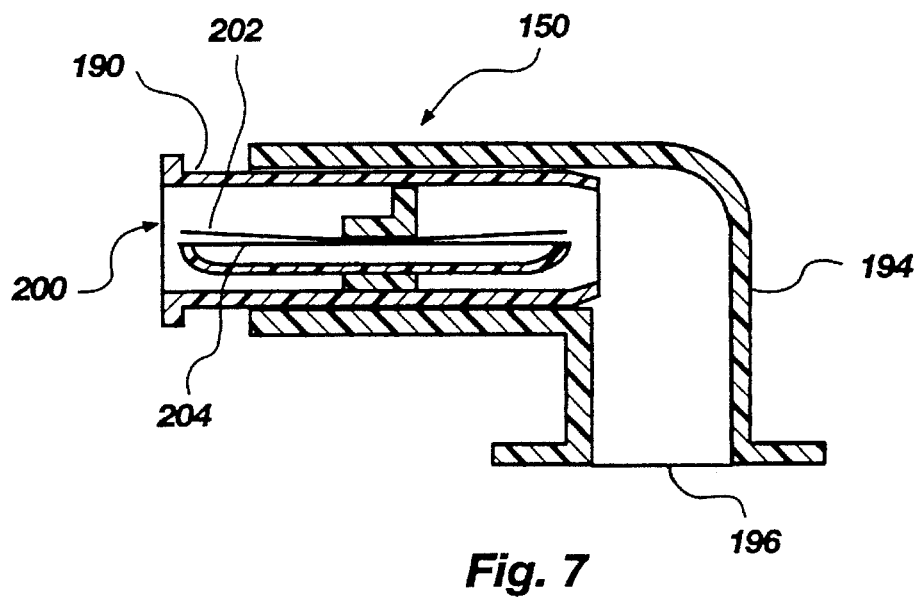
FIG. 7 is a side sectional view of the second embodiment of an audible indicator.

In FIGS. 6A and 6B, the indicator is an audible indicator 150, which is shown in detail in FIG. 7. Various other indicators, including those described and illustrated in detail in this specification could be used instead. As with the system of FIG. 1, if intubation is proper, tip 98 is in the trachea and the system pressure remains essentially constant as plunger 66 is pulled back. Accordingly, there is no pressure differential across indicator 150 even when plunger seal 78 passes orifice 144. By contrast, if it is in the esophagus, tip 98 becomes occluded and the system pressure decreases. When plunger seal 78 passes orifice 144, a significant pressure differential is created across indicator 150 causing activation of indicator 150 (i.e., indicator 150 makes a noise).

Indicator 150 may be held in place by a base 166 that is secured to barrel 140 over orifice 144 with a strap 168. Base 166 and strap 168 are preferably made of rubber or flexible silicone which fits around barrel 140 and forms a hermetic seal with barrel 140. Base 166 and strap 168 may be formed or joined as a unit. Alternatively, base 166 may be glued, welded, or otherwise attached to barrel 140. Orifice 144 may have a stem (similar to luer lock 80 in FIG. 1) connected to it.

Referring to FIGS. 6A and 6B, esophageal intubation detector 134 is connectable to endotracheal tube 16 by means of an adapter 156. Adapter 156 includes an endotracheal tube adapter 158 and a connection tube 162. One end of connection tube 162 is connected to syringe tip 44 and the other end of connection tube 162 is connected to endotracheal tube adapter 158.

Adapters between the syringe and endotracheal tube are desirable in the case in which typical syringe tips are not suitable for connection directly with typical endotracheal tubes. However, the invention is not restricted to systems with adapters. For example, the syringe (or other volume changing devices described below) and/or the endotracheal tube may be constructed such that an adapter is not necessary. That combination could be sold as individual parts or as an integral unit for use by clinicians. The indicator could be attached to the syringe (or other volume changing devices described below) and/or the endotracheal tube.

FIG. 7 shows a cross-section of a side view of audible indicator 150 (shown in FIGS. 6A and 6B), which includes a whistle 190 in a housing 194. Housing 194 includes an orifice 196 which may be aligned with and sealed around (or otherwise formed with respect to) orifice 144. Whistle 190 includes an orifice 200, and reed elements 202 and 204, which create a noise when air passes through them. When tip 98 is occluded and plunger seal 78 passes by orifice 144, air suddenly passes through orifice 200 toward orifices 196 and 144 creating a noise.

Figure 8:
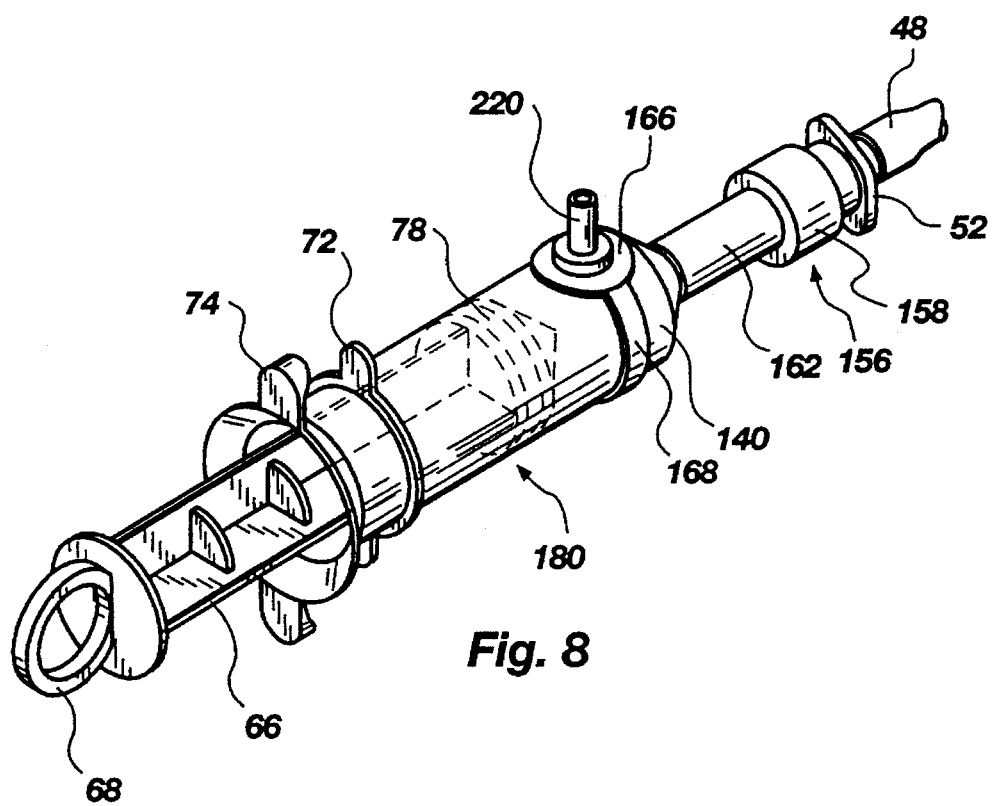
FIG. 8 is a perspective view of a third embodiment of an esophageal intubation detector (like that of the second embodiment shown in FIGS. 6A and 6B except the orifice is closer to the syringe tip) that includes a third embodiment of an audible indicator.

FIG. 8 is a perspective view of a third embodiment of an esophageal intubation detector 180, which is like that of the second embodiment shown in FIGS. 6A and 6B except orifice 144 is closer to the syringe tip. There are some tradeoffs in the choice of positioning orifice 144 with respect to tip 44. The following are factors to consider. First, at least some significant negative pressure is required to properly activate an indicator (e.g., to be sufficiently loud to be heard). This would suggest moving the orifice 144 farther from syringe tip 44 to make a loud noise. Second, the farther orifice 144 is from syringe tip 44, the more effort is required to pull plunger 66 and the greater the reduction in pressure and/or the longer the reduction in pressure. Experimentation may provide information regarding how far orifice 144 should be from tube tip 44. It is expected, however, that a fairly loud noise can be generated with orifice 144 being fairly near tube tip 44 (as shown in FIG. 8).

Figure 9A:
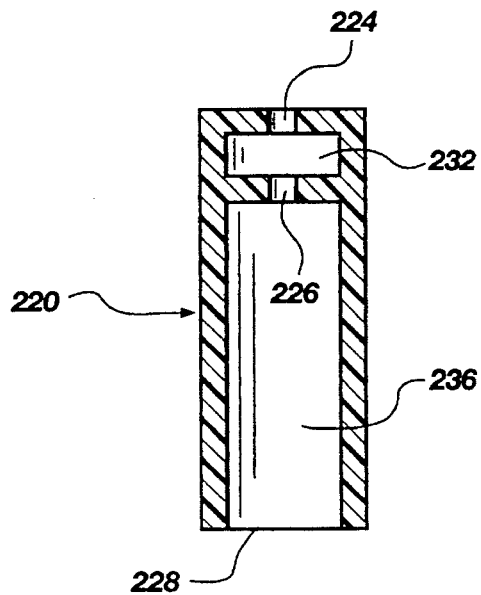
FIG. 9A is a side sectional view of the third embodiment of audible indicator.
Figure 9B:
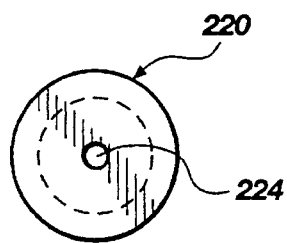
FIG. 9B is a top view of the third embodiment of audible indicator shown in FIG. 9A.

FIGS. 9A and 9B show side and top views of an audible indicator 220 (shown in FIG. 8), which is a third embodiment of an audible indicator. Audible indicator 220 includes small diameter orifices 224 and 226, and a larger diameter orifice 228, which is aligned with and sealed around (or otherwise joined with) orifice 144. Audible indicator 220 includes cavities 232 and 236. If tip 98 is occluded a negative pressure is created. When plunger seal 78 passes by orifice 144, air passes through orifices 224 and 226 toward orifices 228 and 144 causing a sound to be produced. Indicator 220 could be positioned on an adapter, such as in FIG. 1.

Figure 10:
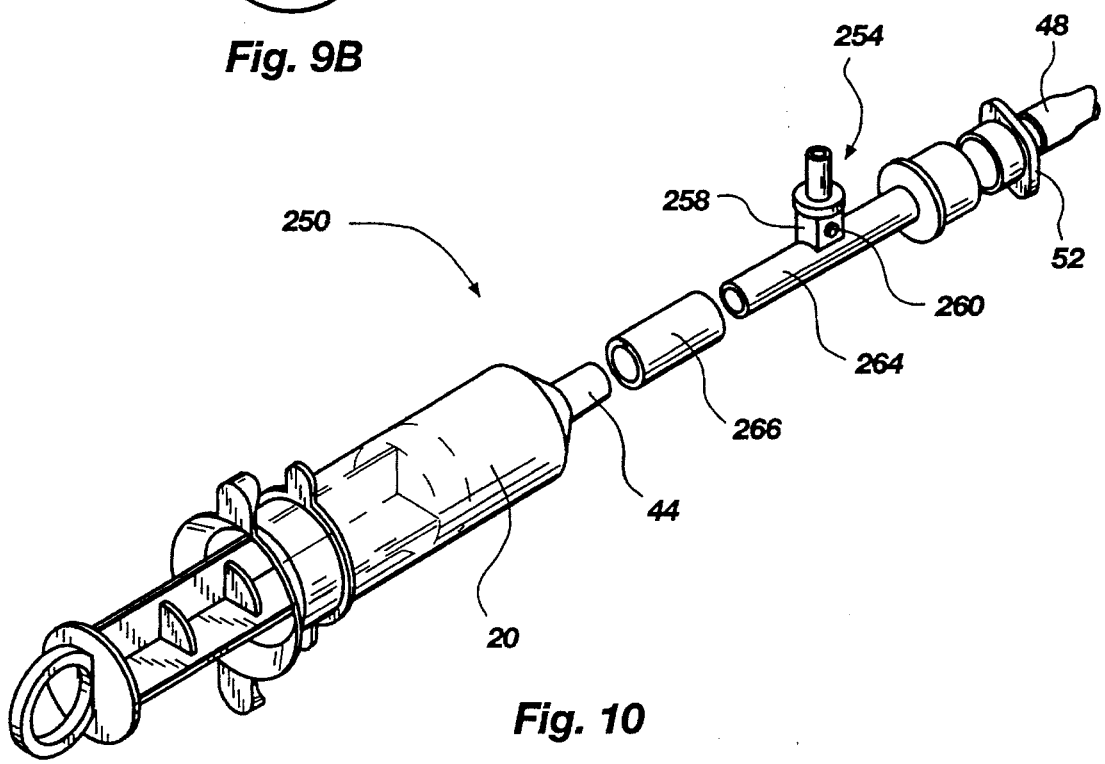
FIG. 10 is an exploded view of a fourth embodiment of an esophageal intubation detector including a fourth embodiment of an audio indicator and connected to an endotracheal tube.

FIG. 10 illustrates esophageal intubation detector 250, which is an alternative arrangement of esophageal intubation detector 14 in FIG. 1. An indicator 254 (which may be the same as audible indicator 220 or a visual indicator) is positioned on a switch housing 258 having a control switch 260. After the system pressure is significantly negative due to pulling back the plunger, the clinician presses a button in control switch 260 allowing air to flow through indicator 254. Activation of control switch 260 is analogous to the crack pressure of indicator 32. An advantage of using switch 260 is that the clinician will know when to expect a noise or visual indication. This may be useful in situations of distracting noise or light. FIG. 10 also illustrates an alternative adapter arrangement including adapter 264 and connector element 266.

Figure 11:
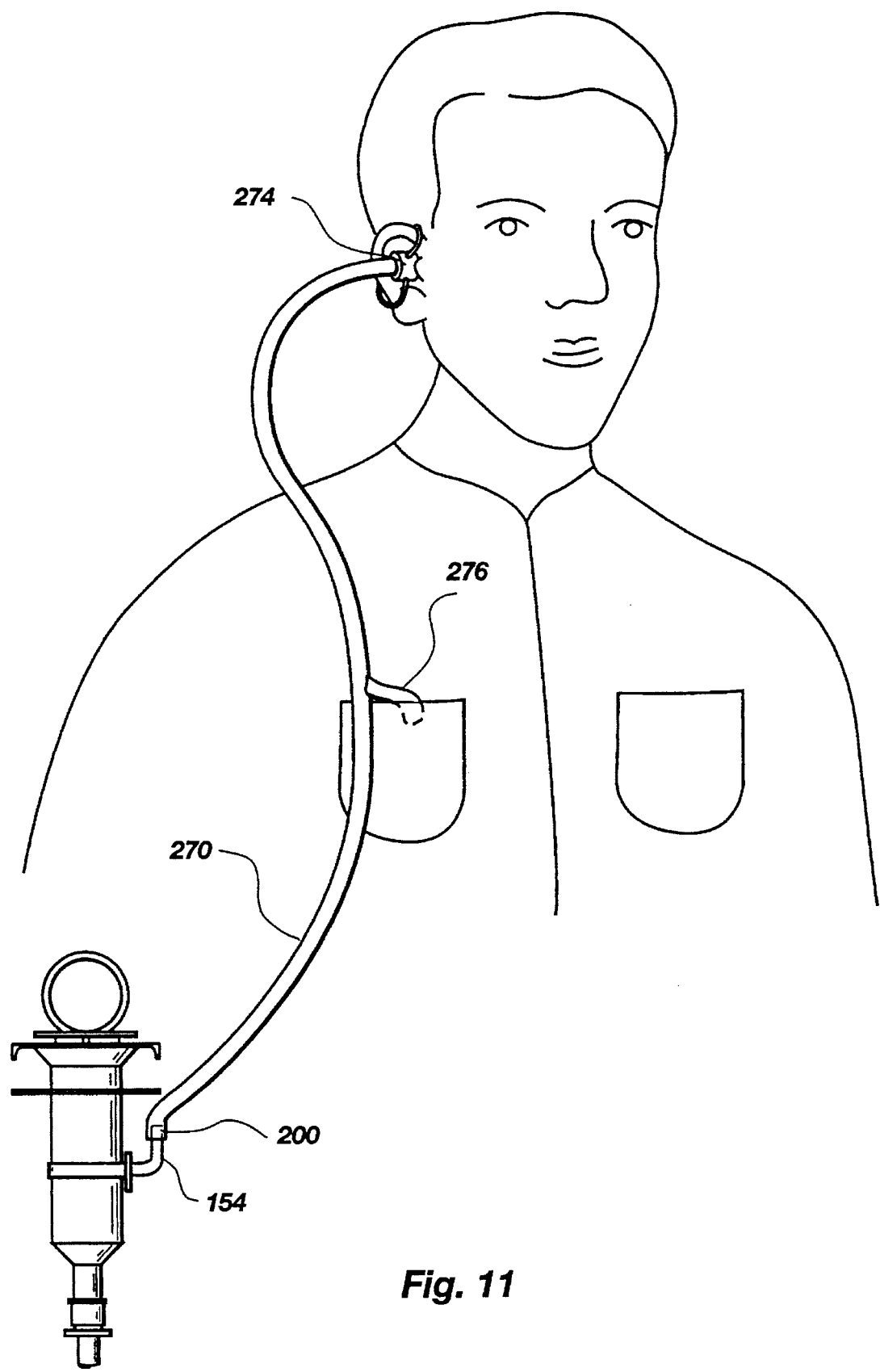
FIG. 11 is a perspective view of an extension tube that connects an audible indicator of an esophageal intubation detector to an ear piece fitting into the ear of a clinician.

Emergency settings in which the esophageal intubation detection systems described herein may be used are often noisy. Referring to FIG. 11, a tube 270 is connected between orifice 200 of audible indicator 154 and an ear piece 274 clipped to the ear of a clinician. A clip 276 may be clipped to the clothing of the clinician to prevent ear piece 274 from being pulled from the clinician's ear. Of course, tube 270 may be used in connection with the other audible indicators.

2. Visual Indicators

As an alternative or addition to an audible indicator, a visual indicator may be used to provide an indication of whether intubation is proper.

Figure 12A:
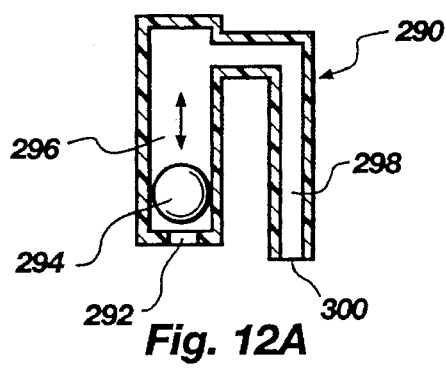
FIG. 12A is a side sectional view of a first embodiment of visual indicator.
Figure 12B:
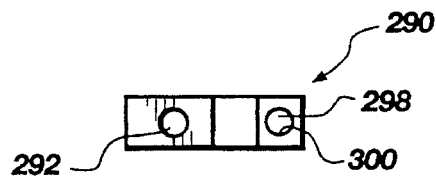
FIG. 12B is a top view of the first embodiment of visual indicator shown in FIG. 12A.

FIGS. 12A and 12B show side and top views of a transparent visual indicator 290, which is a first embodiment of a visual indicator. Visual indicator 290 includes a cavity 296 between an orifice 292 and a tube 298. Tube 298 includes an orifice 300, which is aligned with and sealed around (or otherwise connected to) an orifice in a detection system, such as orifice 82 in FIG. 3 or orifice 144 in FIG. 6B. When a significant pressure differential is created between orifice 292 and orifice 300 (because holes 102A and 102B in tip 98 are occluded), air passes through orifice 292 and toward orifice 300 causing a ball 294 to rise, indicating that tube tip 98 is in the esophagus rather than the trachea. Ball 294 may be made of or covered with glow in the dark material for ease of sight during low light conditions.

Figure 13A:
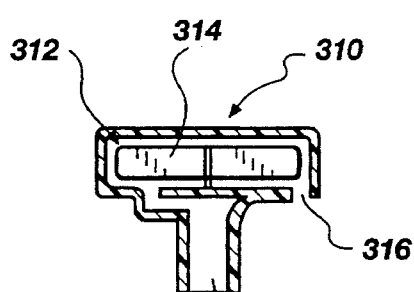
FIG. 13A is a side sectional view of a second embodiment of visual indicator.
Figure 13B:
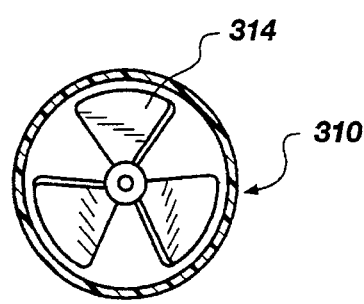
FIG. 13B is a top view of the second embodiment of visual indicator shown in FIG. 13A.

FIGS. 13A and 13B show side and top views of a visual indicator 310, which is a second embodiment of a visual indicator. Visual indicator 310 includes a cavity 312, in which a paddle wheel 314 is suspended, and orifices 316 and 318. Orifice 318 is aligned with and sealed around (or otherwise connected to) an orifice in a detection system, such as orifice 82 in FIG. 3 or orifice 144 in FIG. 6B. When a significant pressure differential is created between orifice 316 and orifice 318 (because holes 102A and 102B in tip 98 are occluded), air passes through orifice 316 toward orifice 318 causing paddle wheel 314 to spin indicating that intubation may have been in the esophagus rather than the trachea. Wheel 314 may be covered with glow in the dark material.

Figure 14A:
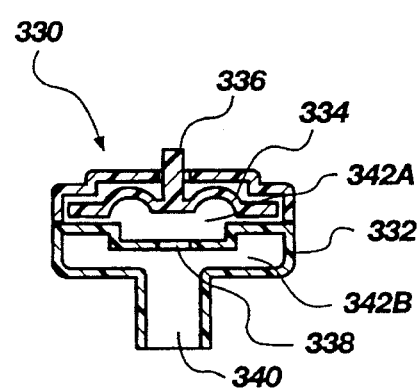
FIG. 14A is a side sectional view of a third embodiment of visual indicator.
Figure 14B:
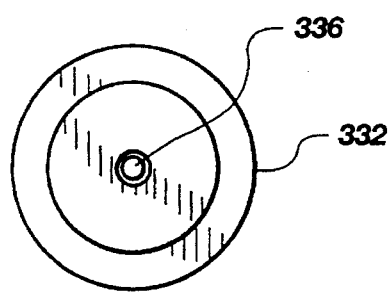
FIG. 14B is a top view of the third embodiment of visual indicator shown in FIG. 14A.
Figure 16:
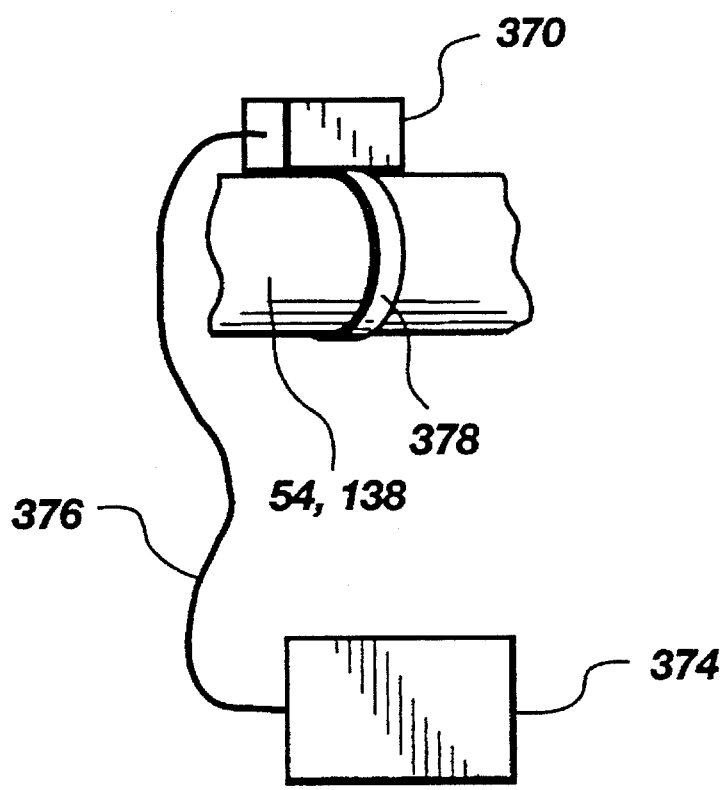
FIG. 16 shows a perspective view of an esophageal intubation detector having a transducer that provides a signal to a communication device.

Indicators 32, 150, 220, 290, and 310 are examples of vented indicators. These indicators are activated by a flow of air from the outside, through them and an orifice in a detection system, such as orifice 82 in FIG. 3 or orifice 144 in FIG. 6B. This flow of air will only occur if endotracheal tip 98 is occluded by the esophagus causing the system pressure to be negative, creating a significant pressure differential across the indicator. The indicators illustrated in FIGS. 14A, 14B, and 16 are examples of non-vented indicators. (It is expected that transducer 370 in FIG. 16 could be vented or non-vented.) Non-vented indicators are activated by the negative pressure causing a significant pressure differential across the indicator, but they do not allow air flow through the indicator.

FIGS. 14A and 14B show side and top views of a visual indicator 330, which is a third embodiment of a visual indicator. Visual indicator 330 includes a housing 332 that encloses a silicone diaphragm 334. An orifice 338 separates cavities 342A and 342B within housing 332. Silicone diaphragm 334 is connected to an indicator post 336. Visual indicator 330 includes an orifice 340, which is aligned with and sealed around (or otherwise connected to) an orifice in a detection system, such as orifice 82 in FIG. 3 or orifice 144 in FIG. 6B. When a significant pressure differential is created between the atmospheric pressure and the pressure at orifice 340 (because holes 102A and 102B in tip 98 are occluded), the pressure inside cavities 342A and 342B suddenly decreases causing silicone diaphragm 334 to pull indicator post 336 toward orifice 340, indicating that the endotracheal tube may have been in the esophagus rather than the trachea. Indicator post 336 may be made of or covered with glow in the dark material. Alternatively, visual indicator 330 could be designed so that indicator post 336 pops up rather than down.

3. Audio and/or Visual Indicators

Figure 15:
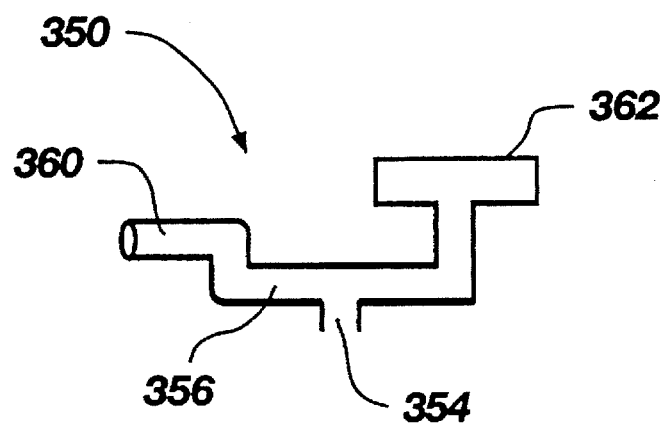
FIG. 15 shows a side view of a combined indicator including both audio and visual indicators.

FIG. 15 shows a combination audio and visual indicator 350. T-connector tube 356 includes an orifice 354, which is aligned with and sealed around (or otherwise connected to) an orifice in a detection system, such as orifice 82 in FIG. 3 or orifice 144 in FIG. 6B. T-connector tube 356 is connected to an audible indicator 360 (which may be any of the above-described audible indicators or another audible indicator) and a visual indicator 362 (which may be any of the above-described visual indicators or another visual indicator). Rather than using a connector tube 356, there could be two orifices, preferably at the same distance from syringe tip 44 (whether on the syringe or adapter), connected to two indicators.

Referring to FIG. 16, the indicator could be a transducer 370 connected to a communication device 374 through a wire 376. Transducer 370 could be activated in response to a change in pressure, a particular pressure differential across the transducer, a particular air speed, flow of air, or some other phenomenon. Communication device 374 could be an audio indicator (such as a loud speaker) and/or a visual display. The visual display could include a liquid crystal display (LCD) or light emitting diodes (LEDs). The LCD could display words describing the condition detected. Information that communication device 374 could provide includes the following: (1) tip 98 is in the esophagus, with the absence of the information indicating the contrary; (2) tip 98 is in the trachea, with the absence of the information indicating the contrary; or (3) tip 98 is in the esophagus or the trachea, depending on the particular situation at the time.

Transducer 370 could include a transmitter, and communication device 374 could include a receiver, such that wire 376 is not required.

Transducer 370 could be connected over an orifice in an adapter (for example, adapter 54 in FIG. 1), in a syringe (for example, syringe 138 in FIG. 6A), or another volume or pressure changing device (such as a bulb or bag described below). Communication device 374 could be also placed right on the adapter or syringe. Various means, such as glue or an optional strap 378 may be used to secure the transducer and/or communication device to the adapter, syringe, or other volume or pressure changing device.

Transducer 370 could include a sound detecting transducer placed over an audible indicator and connected to an amplifier and speaker to provide increased sound.

Transducer 370 could be vented or non-vented. Under one embodiment, if transducer 370 is non-vented, the pressure sensed by it will decrease as the plunger seal is pulled away from the syringe tip. At a pre-defined or particular negative pressure, the transducer will be triggered, indicating that tip 98 is improperly placed. If the transducer is vented, the achievement of this negative pressure will result in sudden flow of air through the orifice and a return in atmospheric pressure, which will also trigger the transducer and indicate improper endotracheal tube location.

An ear clip as in FIG. 11 may be used in connection with a transducer 370.

The preferred location of the indicator orifice (such as orifice 82 in FIG. 3 or orifice 144 in FIG. 6B) in the esophageal intubation detection system depends on the type of indicator used. If indicators requiring a predetermined negative pressure to be activated such as indicators 32, 330 and 370 (described in FIGS. 4A, 4B, 14A, 14B, 16), the preferred location of the orifice will be overlying the adapter such as that shown in FIG. 1. This allows indicator activation at any time the system pressure drops low enough, regardless of the distance plunger 66 has been retraced. Indicators 150, 220, 290 and 310 (described in FIGS. 7, 9A, 9B, 12A, 12B, 13A, 13B) may also be placed in this location provided that, in preferred embodiment they are connected to a pressure sensitive valve such as that used in indicator 32, which will not open until a predetermined (e.g., minus 1.5 to minus 5.0 psi) negative pressure is achieved. If they are used alone as described in FIG. 6B, then orifice 144 should be located on the syringe to allow sufficient negative pressure to be generated prior to orifice 144 being open to the inside of the system. This allows sufficient negative pressure to build up prior to activation of the indicator.

B. Bulb-Based Detection Systems

1. Evacuator Bulb

Figure 17A:
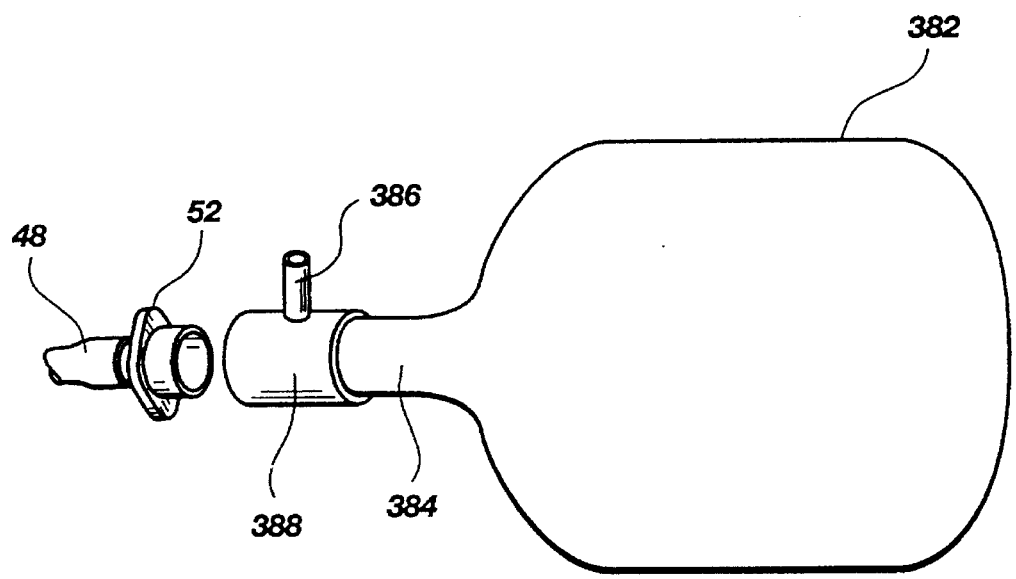
FIG. 17A shows a perspective view of an esophageal intubation detector including an evacuator bulb.

Although the esophageal intubation detector may comprise a syringe, it may use other sources of pressure changes such as a mechanized pump or evacuator bulb. Referring to FIG. 17A, a clinician may use evacuator bulb 382 to change the pressure in an endotracheal tube 48. Indicator 386, which may be any of the previously described indicators, is connected to an adapter 388 through an orifice. Before or after initial intubation, adapter 388 is connected to end adapter 52 at one end of tube 48.

Indicator 386 may also be connected to an orifice anywhere on the bulb where negative pressure is generated. Adapter 388 is located anywhere on bulb 382 where negative pressure is generated. Adapter 388 is connected to evacuator bulb 382 either directly or by a connecting tube 384.

Figure 17B:
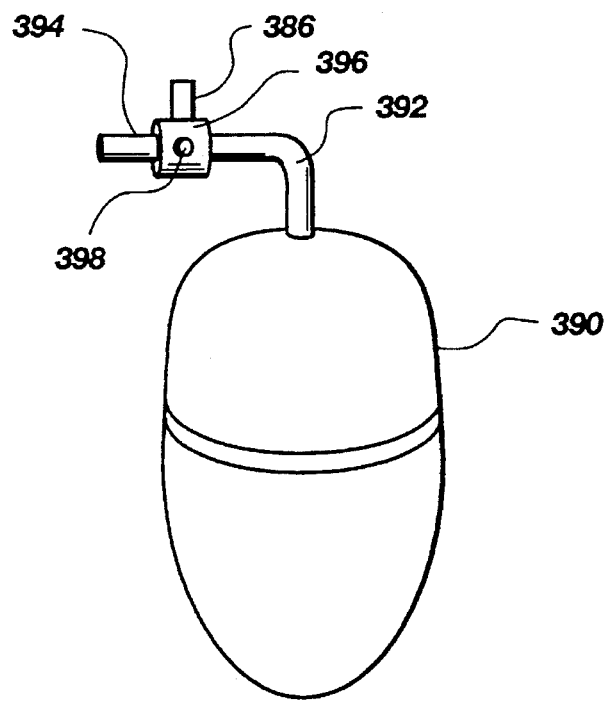
FIG. 17B shows a perspective view of an alternative embodiment of an esophageal intubation detector including an evacuator bulb.

FIG. 17B shows an alternative arrangement of the system of FIG. 17A. Referring to FIG. 17B, evacuator bulb 390 is connected through a tube 392 to a tube 394 through to a switch housing 396. Indicator 386 is connected to switch housing 396. A switch 398 may be used to control flow of air or pressure to which indicator 386 is exposed.

2. Resuscitator Bag

Figure 18A:
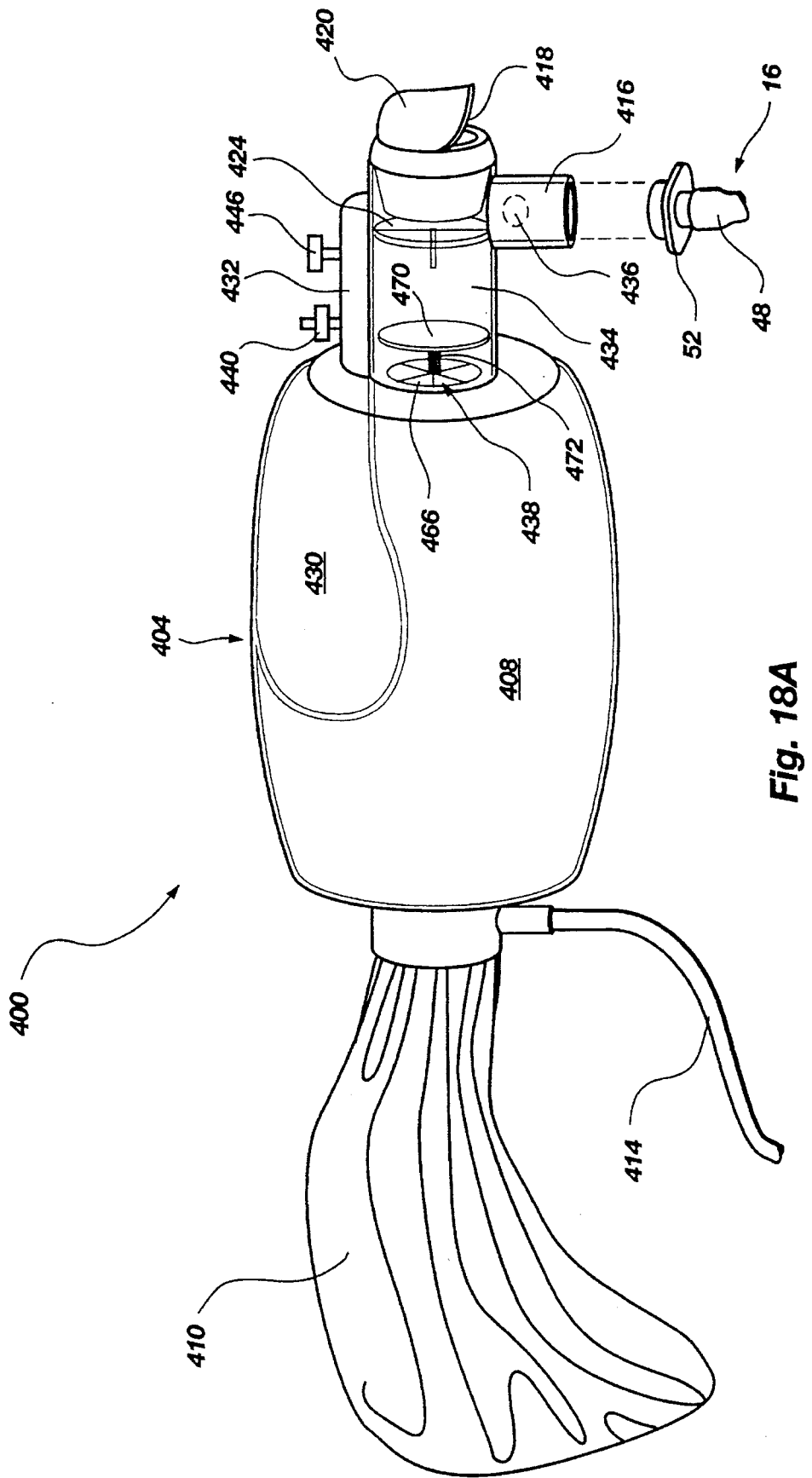
FIG. 18A is a side view of an intubation detector/resuscitator system including an indicator.
Figure 18B:
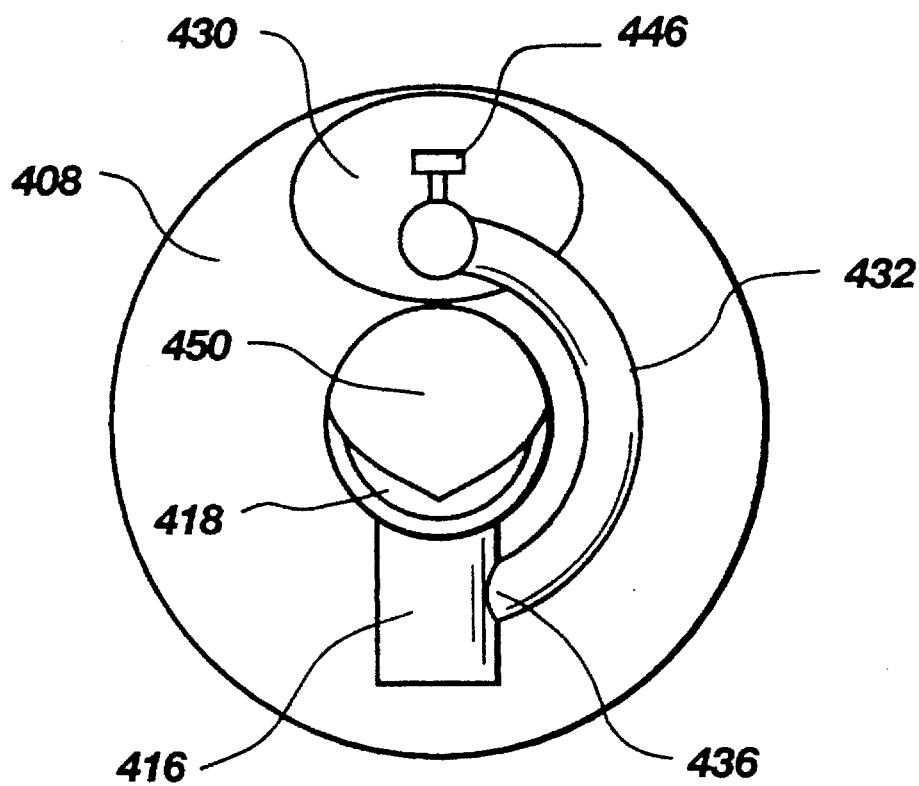
FIG. 18B is a front view of the intubation detector/resuscitator system of FIG. 18A.

Referring to FIG. 18A (side view) and FIG. 18B (front view), in a preferred embodiment, an intubation detection system 400 includes an intubation detection/resuscitator bag 404. In a preferred embodiment, detection/resuscitator bag 404 includes standard, well known parts including a ventilating bag 408, an oxygen reservoir 410, an oxygen tube 414, an adapter 416, an exhalation port 418 through threaded cap 420, and a one-way valve 424 in a cylindrical portion 434. Adapter 416 is attachable and detachable to adapter 52 of endotracheal tube 16. Except as described herein, detection/resuscitator bag 404 may be of the type commonly used by clinicians. Different commercially available resuscitator bags have different types of one-way valves 424. It is believed that many, if not all, of these one-way valves would be acceptable for the present invention.

One embodiment of the present invention includes the following additional components to the standard detection/resuscitator bag 404. An evacuator bulb 430 may be inside or outside, on the top or bottom of ventilating bag 408. A connecting tube 432 connects the evacuator bulb 430 to an orifice 436 in the sidewall of adaptor 416. An indicator 440 is placed on connecting tube 432 or evacuator bulb 430 (or any where negative pressure is generated by evacuator bulb 430). A pressure valve 438 is positioned in cylindrical portion 434 between ventilating bag 408 and adapter 416.

Pressure valve 438 is designed such that oxygen can be easily squeezed through it into endotracheal tube 16 on compression of ventilating bag 408, but oxygen cannot be aspirated through valve 438 when a negative pressure is created by evacuator bulb 430 when tube tip 98 is occluded. If a significant amount of oxygen were to pass from ventilating bag 408 to tube 432, a significant negative pressure would not be created and indicator 440 would not be activated.

One structure for pressure valve 438 includes a spring and is illustrated in FIG. 18A. Under that embodiment, pressure valve 438 includes a spoke opening 466, a plate 470, and a spring 472. Cylindrical portion 434 is separated from bag 408 via spoke opening 466. Plate 470 is connected through spring 472 to the center of spoke opening 466. The diameter of plate 470 is greater than that of spoke opening 466, but less than that of cylindrical portion 434. Therefore, air flow created by squeezing bag 408 pushes plate 470 away from spoke opening 466. When bag 408 is released, plate 470 returns to spoke opening 466 under the force of spring 472. There is no force that causes it to opening again until bag 408 is again squeezed.

Of course, various other configurations could be used. Opening 466 does not have to be a spoke opening.

In a preferred embodiment, the threshold negative opening pressure of pressure valve 438 is greater negative pressure than the negative pressure required to activate indicator 440. For example, in the case where indicator 440 is an audible indicator such as in FIG. 4A, the pressure valve 438 (in the preferred embodiment) would have a higher threshold opening pressure than the "crack" pressure for indicator 440.

A venting on-off switch 446 is positioned within connecting tube 432. With venting switch 446 in the ON position (see FIGS. 19A and 19B), the evacuator bulb is connected via tube 432 to adapter 416 creating an "active" intubation detection system. By turning venting switch 446 to the OFF position (see FIGS. 20A and 20B), evacuator bulb 430 is vented into the atmosphere, resulting in deactivation of intubation detection system 400. Venting switch 446 helps avoid re-insufflation of low oxygen air back into the lungs. Once proper endotracheal tube location is confirmed, venting switch 446 will be turned to the OFF position to deactivate the detection system.

In operation, when intubation detector/resuscitator bag 404 is initially used on a just intubated patient, venting switch 446 will be in the ON position, as shown in FIGS. 19A and 19B. When venting switch 446 is in the ON position, air flows between bulb 430 and adapter 416. End adaptor 52 of endotracheal tube 16 is attached to adapter 416. Bag 408 and bulb 430 are simultaneously compressed through squeezing of the operator's hand. Oxygen is insufflated through barrel 434, out adapter 416 and into the patient via the endotracheal tube tip openings 102A and 102B (see FIG. 1).

Upon relaxation of the operator's hand, bag 408 and bulb 430 begin to spontaneously re-expand due to their preferred structural position in the expanded form. In typically operation, ventilating bag 408 re-expands by aspiration of 100% oxygen out of reservoir 410 (which in turn is refilled by oxygen source through tube 414). Bulb 430, however, cannot refill with oxygen from ventilating bag 408 or reservoir 410 due to pressure valve 438.

Bulb 430 therefore aspirates exhaled air from the patients lungs. If the endotracheal tube tip 98 is located within the patient's trachea, air is aspirated back through endotracheal tube 16 toward orifice 436, connecting tube 432, and bulb 430. The ability for bulb 430 to easily fill with air from the lungs prevents any generation of a "significant" negative pressure and no activation of indicator 440 occurs.

On the other hand, if endotracheal tube tip 98 is located within the esophagus, tube tip 98 becomes occluded as bulb 430 expands and no air is available for aspiration into bulb 430. This results in a "significant" negative pressure generation as bulb 430 attempts to re-expand, which causes activation of indicator 440. This signal warns the operator that the endotracheal tube is improperly located within the esophagus and should be removed and re-inserted properly.

Repeat squeezing of bag 408 and bulb 430 to ventilate the patient results in a similar sequence of events. Once the operator is convinced that the endotracheal tube tip 98 is properly located within the trachea, he or she deactivates the intubation detection system 400 by turning valve venting switch 446 to the OFF position, as shown in FIGS. 20A and 20B. As can be seen in FIGS. 20A and 20B, when venting switch 446 is in the OFF position, an orifice 452 becomes open allowing flow of air between bulb 430 and the outside. This results in air within bulb 430 being squeezed into and re-aspirated from the atmosphere. Deactivation of the detection system (through turning venting switch 446 to the OFF position) prevents continuous re-insufflation of exhaled air (low oxygen, high $CO_2$) back into the patient. The patients exhaled air will now leave via the exhalation port 418 (shown in FIGS. 18A and 18B).

C. Additional Information

The present invention is not limited to use with endotracheal tubes, but may be used with other tubular airway controlling devices such as an esophageal tracheal combitube or a pharyngeal tracheal lumen (PTL) airway.

The indicator may be placed over an orifice in the endotracheal tube (or other tubular airway controlling device) rather than over an orifice in an adapter, syringe or connecting tube 432. That an indicator is "positioned over an orifice" does not mean that the indicator does not also extend into the orifice.

As used herein, the term "pneumatically connected" means that two elements are connected by air at essentially the same air pressure. For example, in FIG. 1, indicator 32 is pneumatically connected to syringe 20 and endotracheal tube 16. In FIGS. 6A and 6B, indicator 150 is pneumatically connected to a portion of syringe 138, adapter 156, and endotracheal tube 16 when plunger seal 78 passes orifice 144. In FIG. 18A, indicator 440 is pneumatically connected to bulb 430. Indicator 440 would still be pneumatically connected to bulb 430 if indicator 440 were positioned directly in bulb 430 rather than being positioned adjacent on tube 432.

An indicator may include both vented (such as in FIGS. 9A and 9B) and non-vented portions (such as disk 120 in FIG. 4A).

As presently contemplated, orifice 144 may be approximately 0.10" (0.00254 meters) in diameter and punched or drilled in the side of the syringe barrel. Adapter section 56B may have a 15 mm inside diameter. Endotracheal tube 16 may be of the type marketed by the Mallinckrodt company of Glens Falls, N.Y., under the catalog number 86353. A preferred syringe is relatively short, has a relatively large handle, and has a volume of at least 60 cc. However, other syringes or sources of negative pressure also would be acceptable.

Various other adapters or adaption systems may be used rather than the illustrated adapter. For example, the adaptor may comprise a single piece or several pieces. Connector tubing may be PVC tubing or shrink wrap tubing, which may be less expensive than PVC. The syringe barrel and adapter may be one molded component.

Although esophageal intubation detector 14 and endotracheal tube 16 are typically not connected until after initial intubation, they may be connected before initial intubation.

In the case where the indicator is an audible indicator, an amplifier could be used to produce sufficient sound.

As used herein, the statement that the endotracheal tube is in the esophagus or the trachea means that a portion of, not all of, the endotracheal tube is in the esophagus or the trachea. Also, if holes 102A and 102B are occluded, tip 98 is said to be occluded. Further, the statement that syringe 20 is connected to endotracheal tube 16 does not require that they be directly connected. Rather, they may be indirectly connected by means of an adapter, such as adapter 40.

The above-described audible indicators are merely intended to provide examples of indicators. It will be apparent to those skilled in the art that various other audible and/or visual indicators may be used.

The present invention may be embodied in specific forms other than those of the preceding description, which are to be considered only as illustrative and not restrictive. Accordingly, the scope of the invention is indicated by the following claims, including equivalents thereof, rather than by the specific embodiments described in the preceding description.

What is claimed is:

1. An intubation detection system for use in determining whether a tip of a tubular airway controlling device is in a patient's esophagus or in the patient's trachea, the system comprising:

the tubular airway controlling device including the tube tip;

a volume changing device connected to the tubular airway controlling device;

an indicator that is pneumatically connected to the volume changing device and that is activated in response to a significant pressure differential across the indicator;

whereby, if the tube tip is in the esophagus, the tube tip becomes occluded as the volume changing device increases in volume creating the significant pressure differential across the indicator which activates the indicator indicating that the tube tip is in the esophagus; and if the tube tip is in the trachea, the tube tip does not become occluded as the volume changing device increases in volume, the significant pressure differential across the indicator is not created, and the indicator is not activated.

2. The system of claim 1 in which the volume changing device is a syringe including a plunger and the volume increases by pulling the plunger.

3. The system of claim 1 in which the volume changing device is a bulb having a first bulb shape to which the bulb returns after being squeezed.

4. The system of claim 3 further comprising a ventilating bag connected to the tubular airway controlling device through a pressure valve, the ventilating bag having a first ventilating bag shape to which the ventilating bag returns after being squeezed, the pressure valve allowing flow of air out of the ventilating bag while the ventilating bag is being squeezed, but not after the ventilating bag has been squeezed and is returning to the first ventilating bag shape.

5. The system of claim 1 in which the indicator is connected adjacent the volume changing device.

6. The system of claim 1 in which the tubular airway controlling device is an endotracheal tube.

7. The system of claim 1 in which a venting ON-OFF switch is placed between the volume changing device and the tubular airway controlling device.

8. The system of claim 1 in which the volume changing device is connected to the tubular airway controlling device through an adapter and the indicator is connected over an orifice in the adapter.

9. The system of claim 8 in which the adapter is connected to the volume changing device and in which the tubular airway controlling device includes an end adapter that attaches to the adapter connected to the volume changing device.

10. The system of claim 1 in which the indicator is connected over an orifice in the tubular airway controlling device.

11. The system of claim 1 in which the indicator includes a sound enhancer that increases sound output.

12. The system of claim 11 in which the sound enhancer includes a tube having a length that maximizes sound output.

13. An intubation detection system for use in determining whether a tip of a tubular airway controlling device is in a patient's esophagus or in the patient's trachea, the system comprising:

the tubular airway controlling device including the tube tip;

a bulb connected to the tubular airway controlling device, the bulb having a first bulb shape to which the bulb returns after being squeezed;

an indicator that is pneumatically connected to the bulb and activated in response to a significant pressure differential across the indicator;

a pressure valve;

a ventilating bag connected to the tubular airway controlling device through the pressure valve, the ventilating bag having a first ventilating bag shape to which the ventilating bag returns after being squeezed, the pressure valve allowing flow of air from the ventilating bag while the ventilating bag is being squeezed, but not after the ventilating bag has been squeezed and is returning to the first ventilating bag shape;

whereby, if the tube tip is in the esophagus, the tube tip becomes occluded as the bulb returns to the first bulb shape creating the significant pressure differential across the indicator which activates the indicator indicating that the tube tip is in the esophagus; and if the tube tip is in the trachea, the tube tip does not become occluded as the bulb returns to the first bulb shape, the significant pressure differential across the indicator is not created, and the indicator is not activated.

14. The system of claim 13 further including a venting switch to disconnect the bulb from the tubular airway controlling device.

15. The system of claim 13 in which the bulb is inside the ventilating bag.

16. The system of claim 13 in which the bulb is connected to the tubular airway controlling device through a connecting tube.

17. The system of claim 16 in which the indicator is positioned over an orifice in the connecting tube.

18. The system of claim 13 in which the indicator is positioned over an orifice in the bulb.

19. An intubation detection system for use in determining whether a tip of a tubular airway controlling device is in a patient's esophagus or in the patient's trachea, the system comprising:

the tubular airway controlling device including the tube tip;

an adapter having a cavity and an orifice;

a syringe connected to the tubular airway controlling device through the adapter, the syringe having a plunger and a barrel with a barrel tip; and an indicator positioned over the orifice of the adapter, the indicator being activated in response to a significant decrease in pressure in the cavity of the adapter;

whereby, if the tube tip is in the esophagus, the tube tip becomes occluded as the syringe plunger is pulled away from the barrel tip causing the pressure in the cavity of the adapter to decrease until the pressure in the cavity has significantly decreased activating the indicator which indicates that the tube tip is in the esophagus; and if the tube tip is in the trachea, the tube tip does not become occluded as the syringe plunger is pulled away from the barrel tip, the pressure in the adapter does not significantly decrease, and the indicator is not activated.

20. The system of claim 19 in which the syringe and adapter are connected through a luer lock.

21. The system of claim 19 in which the indicator includes a tube having a length that maximizes sound output.

22. The system of claim 19 in which the indicator makes an audible sound when activated.

23. An intubation detection system for use in determining and providing an indication of a position of a tip of a tubular airway controlling device in a throat of a patient, the system comprising:

an adapter including an orifice suitable for connection with the tubular airway controlling device;

a volume changing device including a cavity having a volume that is selectively changed, the volume changing device being connected to the adapter; and an indicator pneumatically connected to the adapter, the indicator being activated in response to a change in pressure in the adapter, and the indicator including a communication device that is responsive to whether the indicator is activated and that provides an indication as to the position of the tip in the throat.

24. The system of claim 23 in which the change in pressure occurs because of a flow of gas through the indicator.

25. The system of claim 24 in which the indicator detects the flow of gas and is activated in response to the detection of the flow of gas.

26. The system of claim 24 in which the gas is air.

27. The system of claim 23 in which the communication device is a visual display that provides a visual presentation of whether intubation is proper.

28. The system of claim 27 in which the visual presentation includes words.

29. The system of claim 23 in which the communication device is a visual display that includes lights.

30. The system of claim 23 in which the indicator is directly connected to the adapter.

31. The system of claim 23 in which the indicator is directly connected to the tubular airway controlling device.

32. The system of claim 23 in which the volume changing device has a cylinder and a plunger and in which the volume of the cavity changes as the plunger moves with respect to the cylinder.

33. The system of claim 23 further comprising the tubular airway controlling device and in which the tubular airway controlling device is connected to the orifice of the adapter.

34. The system of claim 33 in which the tip is a first tip and the tubular airway controlling device is an esophageal tracheal combitude including the first tip and a second tip, and in which the indicator provides an indication of whether the second tip is in the patient's esophagus or in the patient's trachea.

35. The system of claim 23 in which if the tip is in the trachea, the indicator indicates that the tip is in the trachea, and if the tip is in the esophagus, the indicator indicates that the tip is in the esophagus.

36. An intubation detection system for use in determining and providing an indication of a position of a tip of a tubular airway controlling device in a throat of a patient, the system comprising:

the tubular airway controlling device;

a pressure changing source connected to the tubular airway controlling device that changes pressure in the tubular airway controlling device depending on the position of the tip in the patient's throat; and an indicator pneumatically connected to the tubular airway controlling device, the indicator being activated in response to a change in pressure in the indicator, and the indicator providing an indication of the position of the tip in the throat of the patient.

37. The system of claim 36 in which the indicator is directly connected to the tubular airway controlling device.

38. The system of claim 36 further comprising an adapter that is connected between the pressure changing source and the tubular airway controlling device, and the indicator being directly connected to the adapter.

39. The system of claim 36 in which the pressure changing source includes a cavity having a volume that is selectively changed.

* * * * *